(12) United States Patent
Graf

(10) Patent No.: US 8,172,880 B2
(45) Date of Patent: May 8, 2012

(54) INTERVERTEBRAL STABILISING DEVICE

(75) Inventor: Henry Graf, Lyons (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 757 days.

(21) Appl. No.: 11/982,761

(22) Filed: Nov. 5, 2007

(65) Prior Publication Data

US 2008/0065078 A1    Mar. 13, 2008

Related U.S. Application Data

(63) Continuation of application No. 10/148,693, filed on Aug. 19, 2002, now Pat. No. 7,291,150.

(30) Foreign Application Priority Data

Dec. 1, 1999   (FR) ..................................... 99 15160
Dec. 29, 1999  (FR) ..................................... 99 16662
May 24, 2000   (FR) ..................................... 00 06640

(51) Int. Cl.
    *A61B 17/70*    (2006.01)
(52) U.S. Cl. ........................................................ 606/257
(58) Field of Classification Search .... 623/17.11–17.16; 606/246, 257, 279
    See application file for complete search history.

(56) References Cited

U.S. PATENT DOCUMENTS

| | | |
|---|---|---|
| 3,316,558 A | 5/1967 | Mortensen |
| 3,648,294 A | 3/1972 | Shahrestani |
| 3,853,311 A | 12/1974 | Kreuzer et al. |
| 4,066,279 A | 1/1978 | Kaptanis |
| 4,458,888 A | 7/1984 | Wolf et al. |
| 4,504,044 A | 3/1985 | Shtarkman |
| 4,509,730 A | 4/1985 | Shtarkman et al. |
| 4,830,346 A | 5/1989 | Eberhard et al. |
| 4,911,718 A | 3/1990 | Lee et al. |
| 4,932,969 A | 6/1990 | Frey et al. |
| 5,002,576 A | 3/1991 | Fuhrmann et al. |
| 5,171,280 A * | 12/1992 | Baumgartner ............. 623/17.12 |
| 5,295,563 A | 3/1994 | Bennett |
| 5,370,697 A | 12/1994 | Baumgartner |
| 5,375,823 A | 12/1994 | Navas |
| 5,376,138 A | 12/1994 | Bouchard et al. |
| 5,458,642 A | 10/1995 | Beer et al. |
| 5,460,355 A | 10/1995 | Danek |
| 5,466,261 A | 11/1995 | Richelsoph |
| 5,480,401 A | 1/1996 | Navas |
| 5,534,030 A | 7/1996 | Navarro et al. |
| 5,540,688 A | 7/1996 | Navas |
| 5,556,431 A | 9/1996 | Buttner-Janz |
| 5,562,737 A | 10/1996 | Graf |
| 5,571,191 A | 11/1996 | Fitz |
| 5,616,142 A | 4/1997 | Yuan et al. |
| 5,658,335 A | 8/1997 | Allen |
| 5,669,909 A | 9/1997 | Zdeblick et al. |

(Continued)

FOREIGN PATENT DOCUMENTS

DE          4323595 C1    7/1993

(Continued)

*Primary Examiner* — Anu Ramana

(57) ABSTRACT

The invention concerns a device comprising an implant (18) designed to be inserted at least partially between the vertebral bodies (4, 4') of two neighboring vertebrae, said implant (18) being adapted to provide to said neighboring vertebral bodies (4, 4') at least one degree of mutual freedom, said device further comprising at least an extra-discal member (20), arranged behind the intervertebral space (12), adapted to damp a movement between said vertebrae (2, 2'), at least in the intervertebral flexion direction.

6 Claims, 7 Drawing Sheets

U.S. PATENT DOCUMENTS

| | | |
|---|---|---|
| 5,674,294 A | 10/1997 | Bainville et al. |
| 5,702,450 A | 12/1997 | Bisserie |
| 5,775,677 A | 7/1998 | Englund |
| 5,860,973 A | 1/1999 | Michelson |
| 5,865,845 A | 2/1999 | Thalgott |
| 5,865,847 A | 2/1999 | Kohrs et al. |
| 5,876,402 A | 3/1999 | Errico |
| 5,961,516 A | 10/1999 | Graf |
| 5,976,187 A | 11/1999 | Richelsoph |
| 6,063,121 A | 5/2000 | Xavier et al. |
| 6,082,508 A | 7/2000 | Davis |
| 6,146,421 A | 11/2000 | Gordon et al. |
| 6,179,874 B1 | 1/2001 | Cauthen |
| 6,224,631 B1 | 5/2001 | Kohrs |
| 6,228,118 B1 | 5/2001 | Gordon |
| 6,258,125 B1 | 7/2001 | Paul et al. |
| 6,322,059 B1 | 11/2001 | Kelm et al. |
| 6,419,706 B1 | 7/2002 | Graf |
| 6,692,495 B1 | 2/2004 | Zacouto |
| 6,835,207 B2 | 12/2004 | Zacouto et al. |
| 7,291,150 B2 | 11/2007 | Graf |
| 2002/0151978 A1 | 10/2002 | Zacouto et al. |
| 2003/0055427 A1 | 3/2003 | Graf |
| 2003/0153912 A1 | 8/2003 | Graf |
| 2004/0116927 A1 | 6/2004 | Graf |
| 2004/0230192 A1 | 11/2004 | Graf |
| 2005/0049708 A1 | 3/2005 | Atkinson et al. |

FOREIGN PATENT DOCUMENTS

| | | |
|---|---|---|
| EP | 0260044 A1 | 8/1987 |
| EP | 0277282 A1 | 10/1987 |
| EP | 0282161 A1 | 9/1988 |
| EP | 0346269 A2 | 6/1989 |
| EP | 0566810 A1 | 4/1992 |
| EP | 0610837 A1 | 7/1994 |
| EP | 0820731 A2 | 1/1998 |
| EP | 0897697 A1 | 2/1999 |
| EP | 0953317 A1 | 11/1999 |
| FR | 2676911 A1 | 12/1992 |
| FR | 2723841 A1 | 8/1994 |
| FR | 2744010 | 8/1997 |
| GB | 1306660 | 2/1973 |
| JP | 6-285-099 | 10/1994 |
| JP | 7008504 | 1/1995 |
| JP | 8-294495 | 11/1996 |
| JP | 10-277070 A2 | 10/1998 |
| JP | 11502437 | 3/1999 |
| JP | 2003/515381 | 5/2003 |
| WO | WO 90/11740 | 10/1990 |
| WO | WO 95/00082 | 1/1995 |
| WO | WO 95/15133 | 8/1995 |
| WO | WO 95/35067 | 12/1995 |
| WO | WO 96/28118 | 9/1996 |
| WO | WO 97/15247 | 1/1997 |
| WO | WO 99/32054 A | 1/1997 |
| WO | WO 97/31517 | 8/1997 |
| WO | WO 97/35529 A | 10/1997 |
| WO | WO 99/05968 | 2/1999 |
| WO | WO 01/30248 A1 | 5/2001 |
| WO | WO 01/39678 A1 | 6/2001 |
| WO | WO 01/49192 A1 | 7/2001 |
| WO | WO 02/00124 A | 1/2002 |
| WO | WO 02/00141 A1 | 1/2002 |
| WO | WO 02/43603 A1 | 6/2002 |

\* cited by examiner

US 8,172,880 B2

INTERVERTEBRAL STABILISING DEVICE

CROSS-REFERENCE TO RELATED APPLICATIONS

This application is a continuation of U.S. patent application Ser. No. 10/148,693, now U.S. Pat. No. 7,291,150, filed on Aug. 19, 2002, which is incorporated herein by reference.

BACKGROUND OF THE INVENTION

The present invention relates to an intervertebral stabilising device.

Such a device is usually intended to replace all or part of an intervertebral disc, when the latter has been destroyed by surgery or by disease.

BRIEF SUMMARY OF THE INVENTION

The invention proposes to produce a stabilising device which, while ensuring a satisfactory freedom of movement between the vertebrae which are adjacent thereto, induces only slight mechanical stresses at the level of the whole of the vertebral chain.

To that end, it has for its object an intervertebral stabilising device intended to join two adjacent vertebrae, characterized in that it comprises an implant intended to be inserted at least partially between the vertebral bodies of the two adjacent vertebrae, said implant being adapted to give said two adjacent vertebral bodies at least one mutual degree of freedom, said device also comprising at least one extra-discal member, disposed to the rear of the intervertebral space, adapted to damp a displacement between said vertebrae, at least in the intervertebral flexion direction.

Where the two adjacent vertebrae present a single degree of freedom, it is question of a degree of freedom in rotation, about a transverse axis of the patient, corresponding to the movements of flexion and of extension of this patient. The or each extra-discal member is adapted to damp a displacement between these adjacent vertebrae at least in the intervertebral flexion direction, in which the patient is leaning forward. This intervertebral flexion corresponds to the extension of each extra-discal member, i.e. to its extension in its principal direction, which is substantially the principal direction of the vertebral chain, viz the vertical when the patient is standing up.

BRIEF DESCRIPTION OF THE SEVERAL VIEWS OF THE DRAWINGS

The invention will be described herein below with reference to the accompanying drawings, given solely by way of non-limiting examples in which.

DETAILED DESCRIPTION OF THE INVENTION

Figure 1:
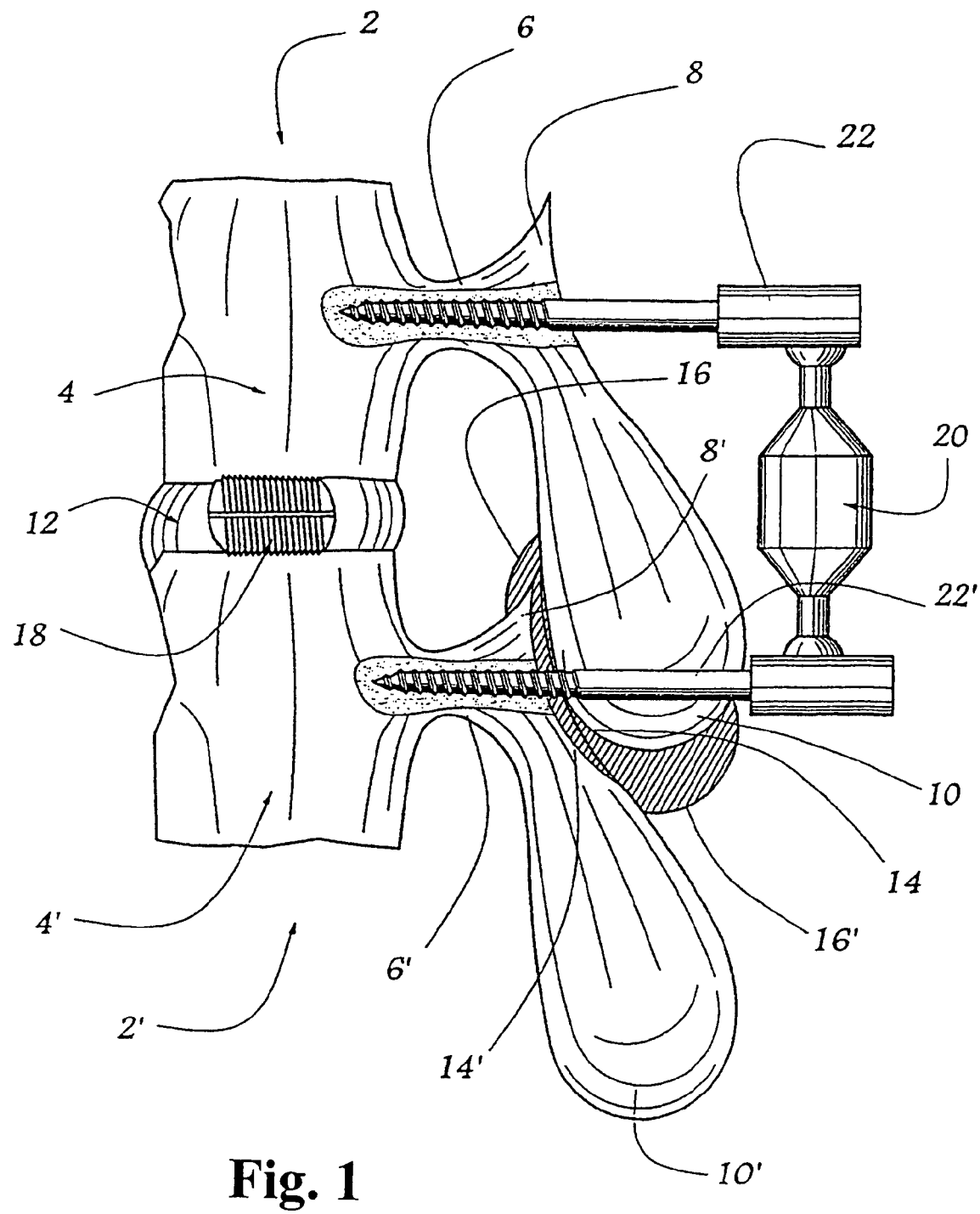
FIG. 1 is a schematic side view, illustrating two adjacent vertebrae between which a stabilising device according to the invention is placed.

FIG. 1 shows two respectively upper (2) and lower (2') vertebrae which are joined via a stabilising device according to the invention. Each vertebra comprises a vertebral body 4, 4' extended by a pedicle 6, 6', an upper articular process 8, 8' and a lower articular process 10, 10'. 12 denotes the intervertebral space, 14 and 14' the opposite articular surfaces, and 16 and 16' the articular capsules.

The two vertebrae 2, 2' are mutually joined via a stabilising device, comprising an intersomatic implant 18, housed in the intervertebral space 12, as well as a damping member, generally designated by reference 20, of which the two ends are fixed on the corresponding vertebrae via pedicular screws 22, 22'.

The damping member is for example in accordance with the teaching of FR-A-2 676 911, or with that of FR-A-2 751 864. It may also comprise a ligament, in accordance for example with the teaching of FR-A-2 694 182.

Figure 2:
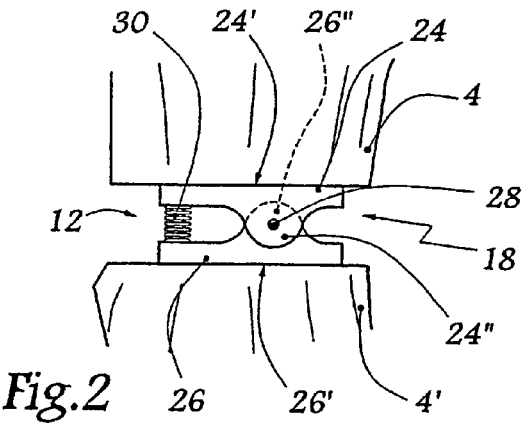
FIG. 2 is a side view, on a larger scale, illustrating an implant belonging to the stabilising device of FIG. 1.

The implant 18 is shown more precisely in FIG. 2. In this latter, as in the following Figures, the right side corresponds to the posterior part of the intervertebral space 12, the left side corresponding to the anterior part.

The implant 18 comprises respectively upper (24) and lower (26) elements coming into contact with the vertebral bodies 4, 4', by respective contact surfaces 24', 26' which are planar. By way of variant, these contact surfaces may be of different shapes, particularly convex.

Elements 24, 26 comprise respective cheeks 24", 26", which are articulated by means of a pivot 28 extending transversely. This pivot 28, which is disposed on the posterior side of the intervertebral space 12, gives a degree of freedom between the surfaces 24' and 26', and therefore between the vertebral bodies 4, 4'. This single degree of freedom is a rotation about the tranverse, or sagittal, pivot 28 or to an extension, this thus corresponding to a flexion of the patient towards the front of the latter towards the rear.

A spring 30, working in compression, is fixed to the elements 24, 26, on the anterior side of the intervertebral space 12. This spring may be replaced by a resilient block, made for example of elastomer, particularly rubber.

Figure 3:
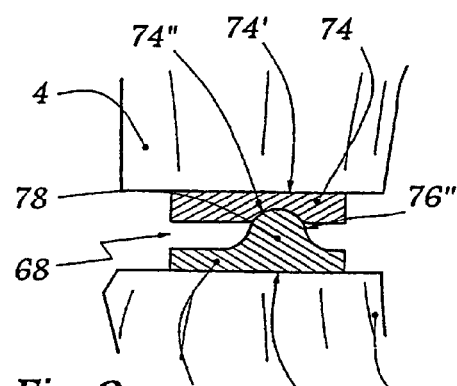
FIG. 3 to 6 are views similar to FIG. 2, illustrating variant embodiments of the implant belonging to the stabilising device of FIG. 1.

FIG. 3 illustrates a second embodiment of the intervertebral implant, designated by reference 68. The latter comprises two respectively upper (74) and lower (76) elements, coming into contact with the vertebral bodies 4, 4' via planar contact surfaces 74', 76'.

One of these elements, in the present case the upper element, is provided with a spherical housing 74", forming cupule, disposed towards the posterior part of the intervertebral space 12. This housing 74" cooperates with a spherical projection 76" of the other element, namely the lower element 76.

Being given that the radii of the housing 74" and of the projection 76" are substantially identical, their cooperation ensures three degrees of freedom in rotation, about the fixed centre 78 of the spherical projection 76", of the contact surfaces 74', 76' and therefore of the vertebral bodies 4, 4'.

It is possible to provide this implant 68 with one or more springs, similar to that, 30, or with a resilient block, extending between the upper and lower elements, for example on the anterior side of the intervertebral space.

Figure 4:
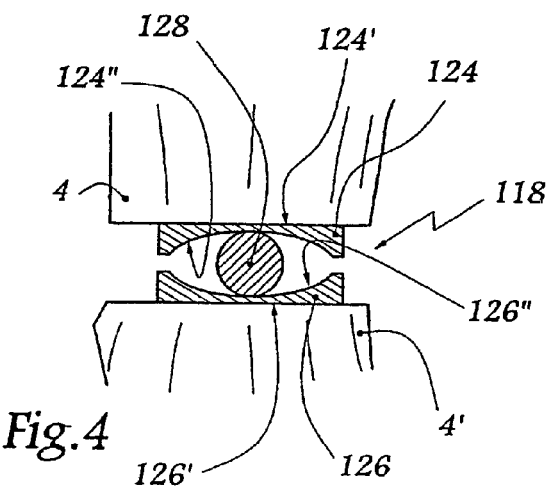

FIG. 4 illustrates a third embodiment of the intervertebral implant, which is generally designed by reference 118. This implant comprises two upper (124) and lower (126) elements forming plates. Each of these plates, which abuts against a respective vertebral body via a planar surface 124', 126', is provided with a spherical recess 124", 126". A ball 128 which presents a radius of curvature substantially smaller than that of the recesses 124", 126", is intercalated between the plates 124, 126.

This ball 128 is free to move in the vicinity of the adjacent surface of the plates 124, 126, which gives three degrees of freedom in rotation to the two vertebral bodies 4, 4' about a mobile point, as well as two degrees of freedom in translation allowed by the slidings of the plates on this ball. The latter may be replaced by a non-spherical member, for example oval or cylindrical, abutting against the plates 124, 126 via a contact surface of which the radius of curvature is less than that of the afore-mentioned recesses 124", 126", in order to allow a mutual displacement of this member with respect to the plate.

Figure 5:
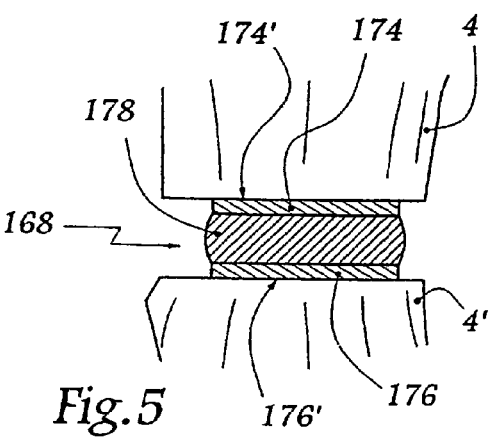

FIG. 5 shows a fourth variant embodiment of the intervertebral implant, generally designated by reference 168. This latter comprises a coating, formed by two rigid plates 74, 176, between which an elastic core 178 is intercalated. The plates 174, 176 partially cover the core 178, in that they are disposed on the edges of this core adjacent the vertebral bodies. The plates are for example made of titanium while the core, which is for example glued to the plate, is made for example of silicone or elastomer, particularly rubber.

The plates 174, 176 come into contact with the vertebral bodies 4, 4' via planar surfaces 174', 176'. This implant is inserted in the intervertebral space by impaction, like implants 18, 68 and 118. It can also be envisaged that the distance separating the contact surfaces 174', 176', which corresponds to the vertical dimension of the placed implant, increases towards its anterior part, in the vertical anatomic rest position of the patient.

Figure 6:
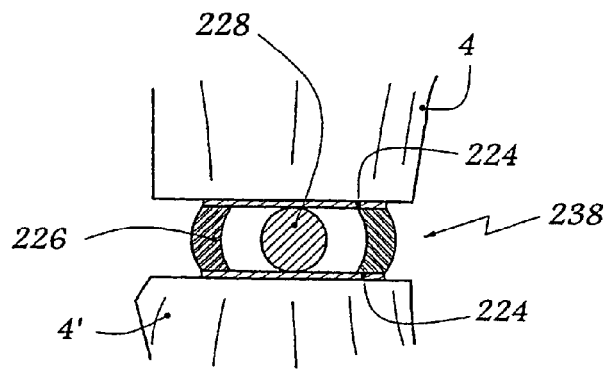

FIG. 6 illustrates a fifth embodiment of the intervertebral implant, generally designated by reference 218. The latter comprises a rigid ball 228 surrounded by a peripheral ring 226, whose principal axis is parallel to the principal axis of the spine, this ring being made of an elastic material such as rubber. The lateral ends of the ring are fast with plates 224 which come into contact with the respective vertebral bodies 4, 4'.

Figure 7:
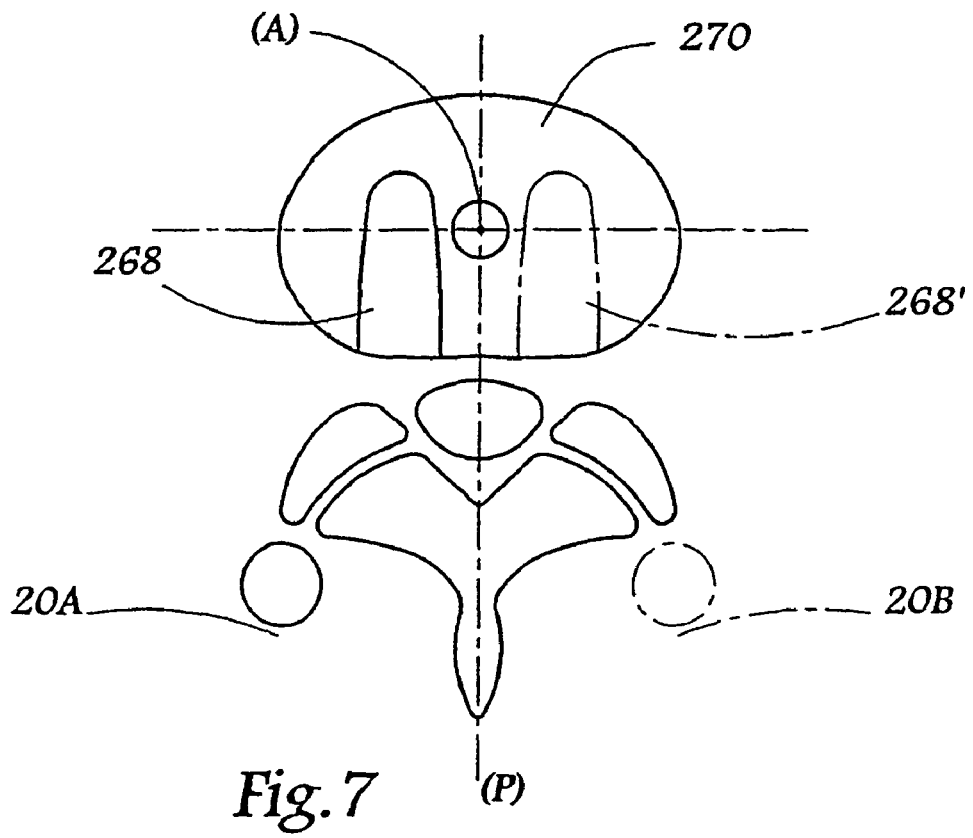
FIG. 7 is a plan view, illustrating an additional variant of the invention.

The implants 18, 68, 118, 168, 218 described hereinabove are complete disc prostheses. It is also possible to employ an implant 268, illustrated in FIG. 7, which is a partial disc prosthesis. The latter 268, which is inserted in the disc 270, is disposed in offset manner with respect to the principal axis A of the vertebral chain which, when the patient is in standing position, is a vertical axis passing through the median plane P extending from the rear of the patient to the front. This prosthesis may be inserted by screwing or impaction in the intervertebral space.

This partial prosthesis 268 is associated with a damping member 20A which is disposed in offset manner on the same side of the axis A as the partial prosthesis 268.

There may be associated with the partial prosthesis 268 an additional prosthesis 268', located on the other side of the axis A. This partial prosthesis 268', which is shown in broken lines, may be similar to the partial prosthesis 268, it being understood that it is possible to give these two partial prostheses 268, 268' different heights, so as to compensate a possible collapse of the disc produced asymmetrically, seen from behind. The partial prosthesis 268' is associated with an additional damping member 20B, shown in broken lines, which is provided on the same side of the axis A as the partial prosthesis 268'.

Figure 8:
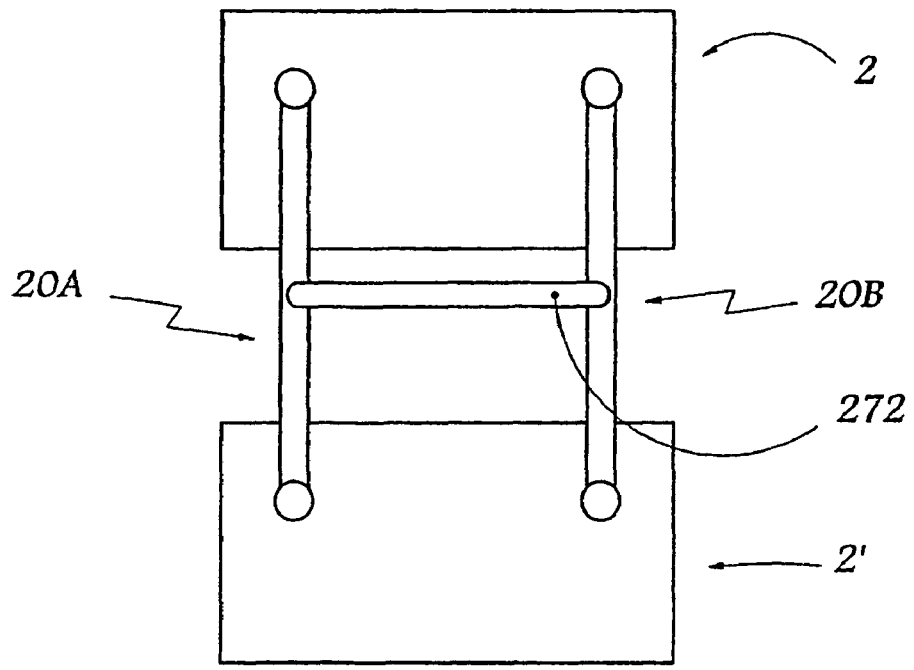
FIG. 8 is a rear view, illustrating the two damping members belonging to the stabilising device of FIG. 7.

FIG. 8 shows the two damping members 20A, 20B disposed on either side of the articular processes 8, 10. These damping members present a metallic part and are for example in accordance with the teaching of FR-A-2 751 864. They are advantageously connected to each other by means of a transverse rod 272, extending substantially horizontally. The connection between each member 10, 10A and the rod 272 is rigid, and for example employs a solder. It is advantageously made at the level of the median part of these damping members.

Figure 9:
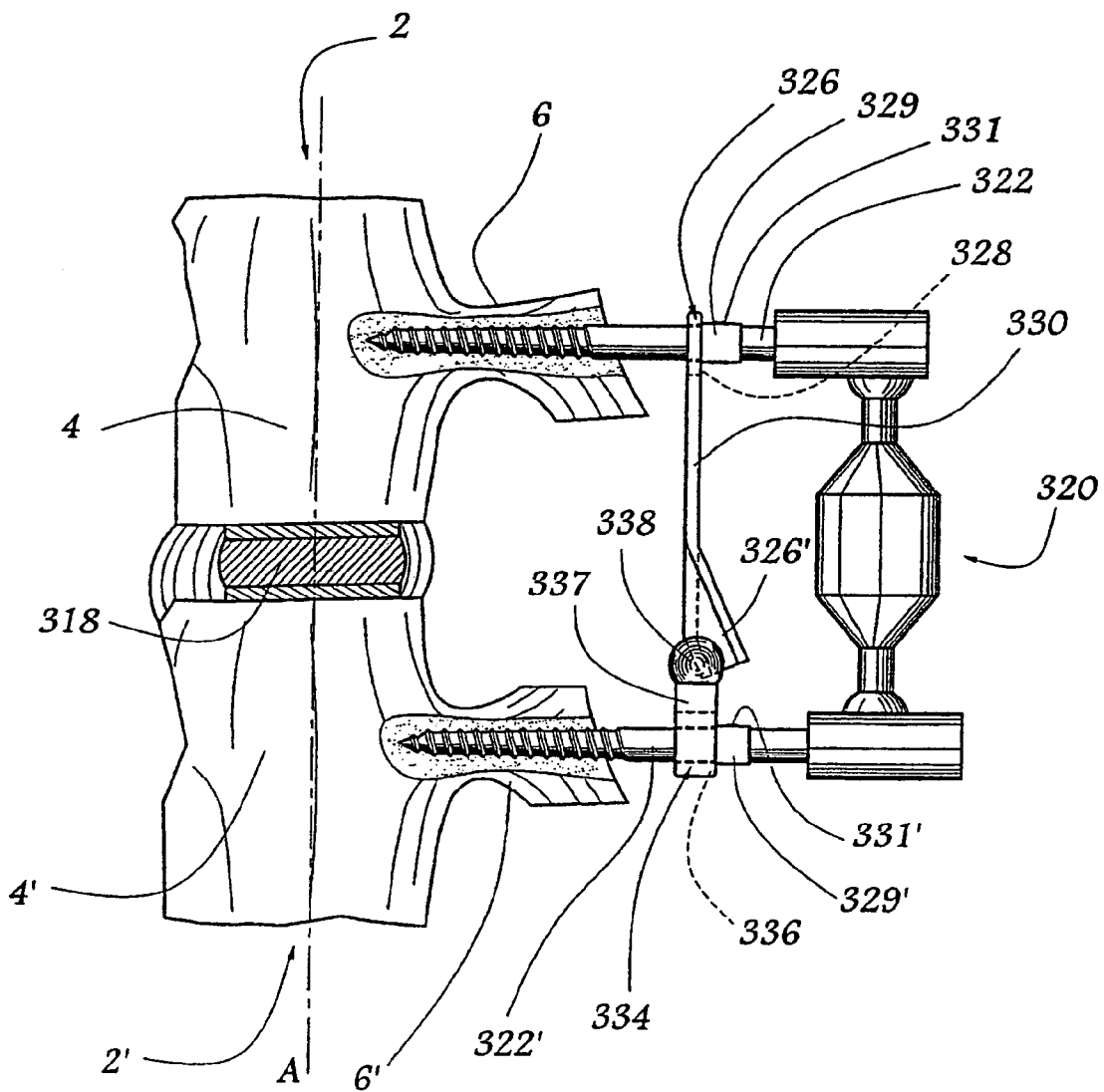
FIG. 9 is a schematic side view, similar to FIG. 1, illustrating an additional variant embodiment of the invention.
Figure 10:
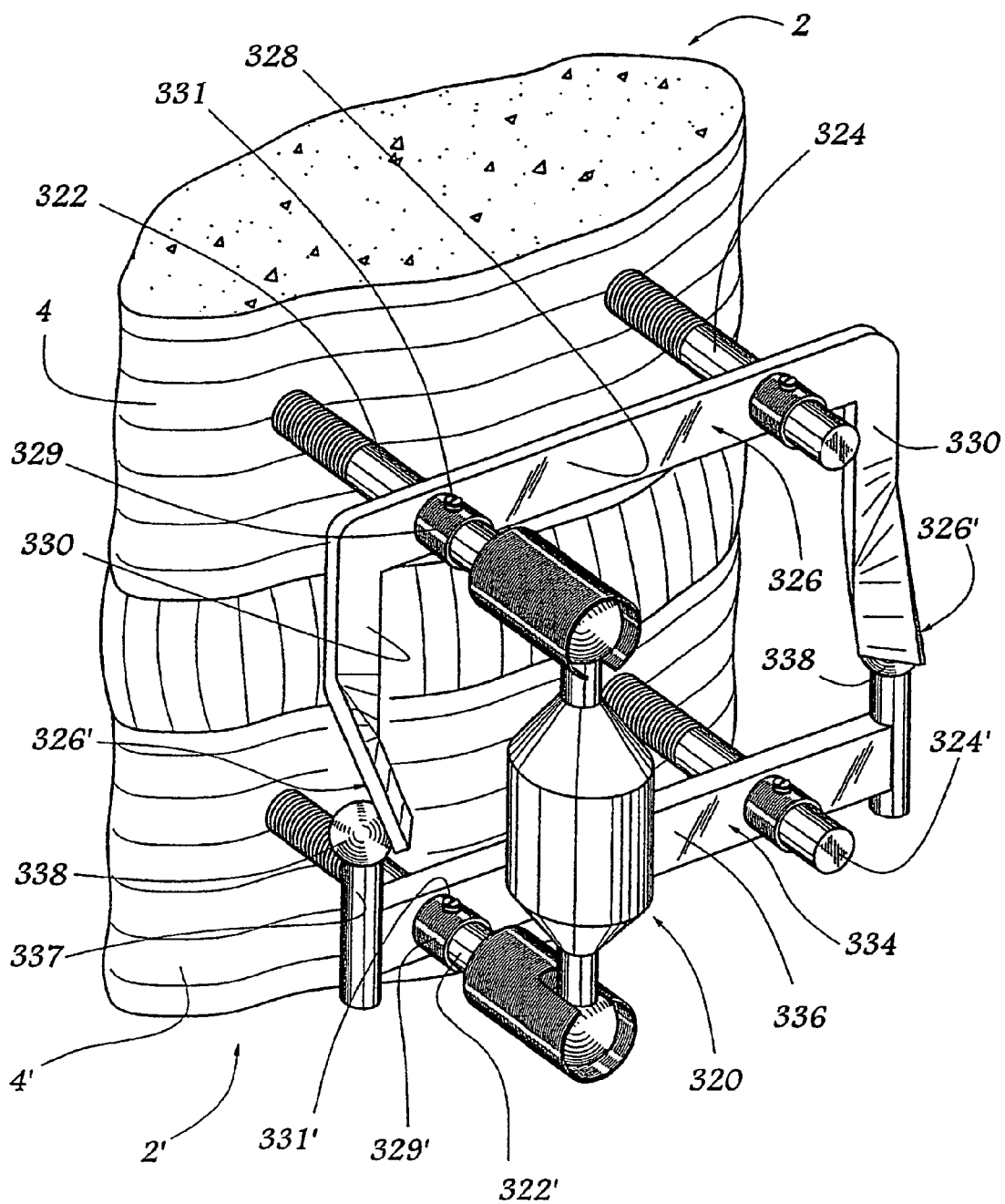
FIG. 10 is a view in perspective, illustrating the device of FIG. 9.
Figure 11:
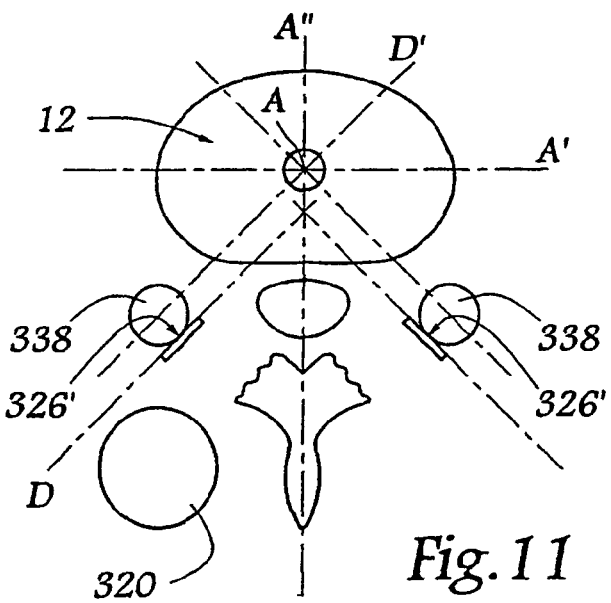
FIG. 11 to 13 are plan views, illustrating the device of FIG. 9, then two variant embodiments.

FIG. 9 to 11 illustrate an additional variant of the invention, in which two upper pedicular screws 322, 324 are provided, disposed on either side of the principal axis of the spine, as well as two lower pedicular screws 322', 324'. The stabilising device comprises an implant 318, for example similar to that, 168, as well as an extra-discal member 320, which is similar to that, 20.

This stabilising device also comprises an upper stop element 326, presenting a horizontal branch 328 as well as two vertical branches 330. This branch 328 has two circular openings hollowed out therein, intended for the passage of the shank of the upper pedicular screws 322, 324. The walls of each opening are extended by an axial sleeve 329, covering a part of the screw. This sleeve, which may be integral with the branch 328, receives a locking screw 331 adapted selectively to immobilize the stop element with respect to the pedicular screw, in a translation parallel to the principal axis of the latter.

This device also comprises a lower stop element 334 comprising a horizontal branch 336 extended, at its two ends, by rods 337 provided with spheres 338. This lower element has two openings hollowed out therein, intended for the passage of the shank of the two lower pedicular screws 322', 324'. Similarly to what has been described hereinabove for the upper element, each opening is provided with an axial sleeve 329' provided with a screw 331'.

Furthermore, in a variant, at least one of the openings may be an oblong slot. This thus makes it possible to adapt the dimensions of the stop elements to different spaced apart relationships of the pedicular screws. The horizontal branches 328 and 336 may present variable lengths, being for example telescopic.

Each vertical branch 330 is bent so that its end presents a planar surface 326' extending obliquely. This means that this end is neither parallel to the median transverse axis A', extending from the right of the patient to left, nor parallel to the median sagittal axis A" extending from the rear of the patient to the front (FIG. 11). The principal axis D of this planar surface 326' is parallel to a straight line D' passing through the intersection of these two axes A' and A", particularly a bisectrix.

Each surface 326' cooperates with a corresponding sphere 338, with a substantially punctual contact. Consequently, two rotations about axes A' and A" are allowed between the upper and lower stop elements and, on doing so, between the two vertebrae 2 and 2'. On the contrary, rotation about the vertical axis A is prohibited between these vertebrae.

Furthermore, mutual translation of the two vertebrae 2, 2' along sagittal axis A" is allowed in one direction. For example, the upper vertebra cannot move forwardly with respect to the lower vertebra, but, on the contrary, is free to move rearwardly with respect to this lower vertebra.

In addition, any mutual translation of the two vertebrae 2, 2' is prohibited, in both directions, along the transverse axis A'. Finally, a mutual translation between these two vertebrae is allowed, in the two directions, along vertical axis A.

Figure 12:
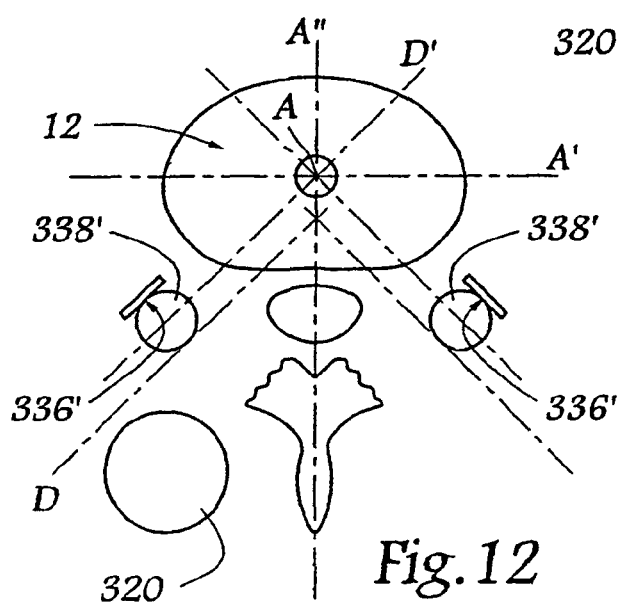
Figure 13:
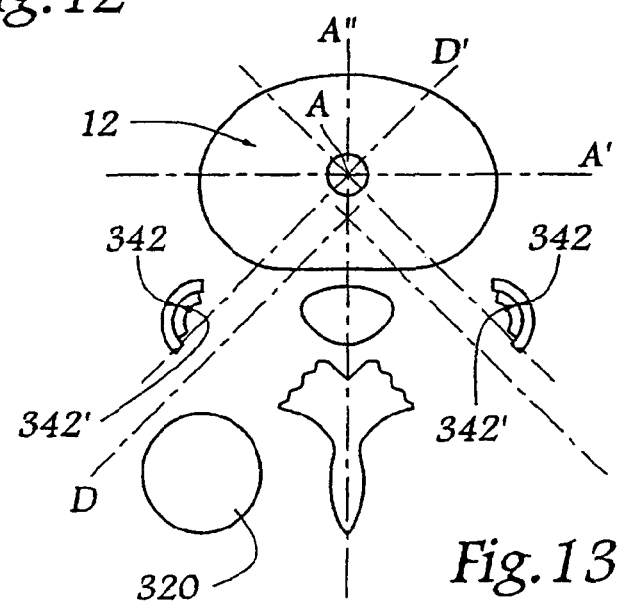

Other arrangements may be envisaged. For example, the upper stop element may be provided with at least one sphere 338', cooperating with a vertical branch, terminated by an oblique planar surface 336', extending from the horizontal branch 336 of the lower element (FIG. 12). The cooperation of two adjacent spherical bearing surfaces 342, 342', of which each belongs to a respective stop element, may be employed (FIG. 13).

By way of additional variant, at least one of the vertical branches 330 may, at least partially, be made of an elastic material, whose elasticity allows a permanent contact between each branch 330 and a corresponding sphere 338. It may also be envisaged to make at least one vertical branch in two parts, presenting a certain mutual clearance in rotation, about the principal axis of the branch. This possibility of clearance may be temporary, for the positioning of the two stop elements, or permanent in order to ensure at each instant an angular adaptation between the branch and the sphere.

It is possible to provide a single vertical branch 330, cooperating with a single sphere 338, particularly in the case of a part of the natural posterior articulation not having been destroyed.

Being given that each upper or lower element is mounted on two pedicular screws at once, this makes it possible to avoid any disconnection of these screws with respect to the vertebral bodies, once said screws are placed in position.

Figure 14:
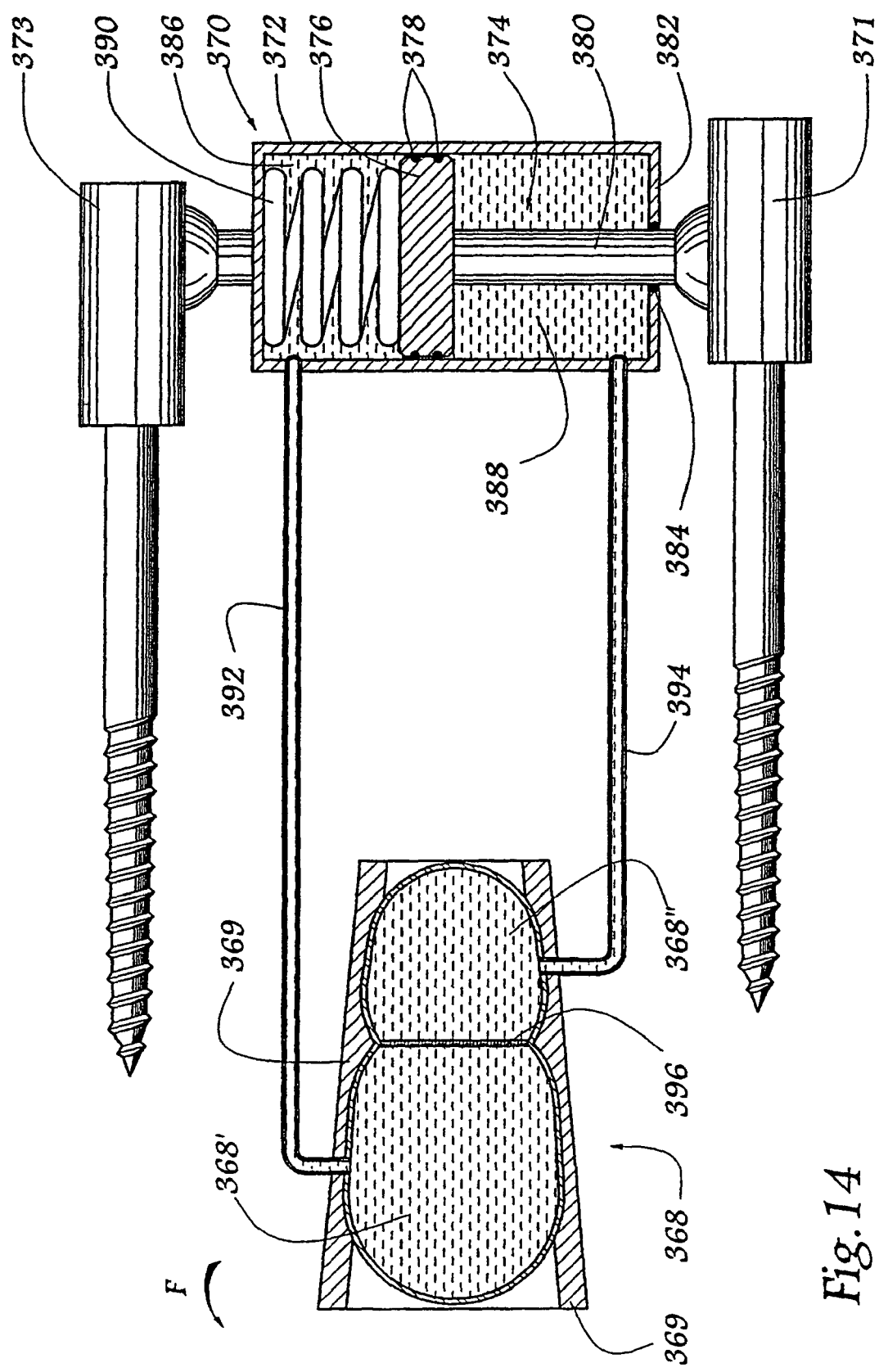
FIG. 14 is a side view illustrating a last variant embodiment of the invention.

FIG. 14 illustrates an additional variant embodiment of the invention. The device which is described therein comprises an implant 368 intended to be inserted at least partially in the intervertebral space. This implant comprises two chambers, respectively front 368' and rear 368", surrounded by two shells 369. Each of these latter, which presents a transverse section substantially in the form of an arc of circle, is made of a rigid material, such as titanium. These shells 369, which are intended to come into contact with the vertebral bodies 4, 4', are fastened to the chambers, for example by gluing.

These two chambers 368, 368', which are separated by a possibly porous membrane 396, are filled with a damping fluid. This latter comprises at least one liquid, such as water or oil. It may also contain air, or even a hydrophilic body such as hydrogel.

The stabilising device illustrated in this FIG. 11 also comprises a damping member 370, disposed to the rear of the intervertebral space. This member comprises a rigid vessel 372 inside which is disposed a piston 374 which comprises a head 376, forming upper end, of which the transverse dimensions are close to those of the vessel. An O-ring 378 is mounted between the opposite walls of the head and of the vessel.

The head 376 of the piston extends from a vertical rod 380 which hermetically traverses the lower wall 382 of the vessel 372, with the interposition of an O-ring 384. The lower end of the rod 380, opposite the head 376, is mounted to pivot on the head of the lower screw 371.

The head of the piston defines respectively upper (386) and lower (388) chambers, belonging to the vessel 372. The upper chamber receives a spring 390, working in compression, which extends vertically between the upper wall of the vessel and the opposite wall of the head. This spring allows the return of the piston into its lower position, which corresponds to a physiologically advantageous lordosic posture of the patient.

The front chamber of the implant 368 is placed in fluidic communication with the upper chamber of the member 370, via a conduit 392, while the rear chamber of the implant is placed in fluidic communication with the lower chamber 388 via an additional conduit 394. Consequently, when the patient leans forward, in the direction of arrow F, fluid is driven out of the front chamber in the direction of the upper chamber, which contributes to causing the piston 374 to descend in the vessel, opposite the upper screw 373. This rise induces a displacement of fluid, via conduit 394, from the lower chamber towards the rear chamber. This movement of flexion is therefore damped by these different flows of fluid.

The invention is not limited to the examples described and shown.

The implant belonging to the stabilising device of the invention may be partial or complete. In the case of it being question of a partial implant, a plurality of implants of this type may be disposed between the same two vertebrae. This implant may be placed in position either by the anterior route or by the posterior route.

Furthermore, it may be provided to use a single ball, similar to that 228, which gives the vertebral bodies 4, 4' three degrees of freedom in rotation, as well as two degrees of freedom in translation. It is also possible to make the intervertebral implant in the form of an envelope containing a hydrophilic gel or water, this implant constituting a nucleus prosthesis.

It is also possible to fix the implant on the vertical wall of the vertebral bodies, for example by screwing, in accordance with the teaching of EP-A-0 346 269, this implant in that case being inserted only partially between the two vertebral bodies.

The intervertebral implant may contain a damping fluid and be in accordance with one of the forms of embodiment described in the French Patent Application filed on Dec. 29, 1999 under No. 99 16662. This fluidic intervertebral implant is capable of cooperating with an extra-discal member of mechanical type, for example similar to that 20.

Furthermore, the extra-discal member may also contain such a damping fluid, and be in accordance with one of the forms of embodiment described in the afore-mentioned French Patent Application. This fluidic extra-discal member is capable of cooperating with a mechanical intervertebral implant such as for example that 18.

The invention makes it possible to attain the objectives mentioned previously.

In the case of degenerative pathology of the intervertebral disc, extending to the nerves which are adjacent thereto, it is necessary for the surgeon to release the nerve root thus compressed. To that end, the corresponding operation induces an at least partial destruction of the posterior intervertebral articulation.

The device of the invention makes it possible to restore the posterior stability, which had been substantially decreased due to the surgery.

The intervertebral implant makes it possible to restore the height of the disc and to recall the natural intervertebral movement, being given that it gives at least one degree of freedom to the vertebral bodies opposite. Furthermore the extra-discal damping member guarantees an additional component for this posterior stabilisation.

The fact of combining this intervertebral implant and this extra-discal member makes it possible to produce these two elements simply and reliably. It is thus possible to distribute, between these two elements, the different mechanical functions which are necessary with a view to ensuring a satisfactory intervertebral stability. This therefore makes it possible to reduce the mechanical stresses exerted on each of these two elements, with the result that these latter are subjected to restricted wear. This therefore prolongs the life duration accordingly.

The stabilising device of the invention thus guarantees that the relative movement of the two vertebrae which it connects is sufficiently close to the movement allowed by a natural vertebral disc, for no major dysfunction to appear at the level of the whole of the vertebral chain.

The use of two extra-discal damping members, disposed on either side of a principal axis of the spine, is advantageous. In effect, it ensures an additional damping component, when the patient is leaning on the sides.

It is advantageous to provide means for connection between these two damping members, insofar as this ensures a substantial reduction of the intervertebral horizontal shear, as in the case of break or absence of one or of two posterior articular masses.

It is advantageous to make the intervertebral implant in the form of at least one partial prosthesis. In effect, such prostheses, due to their dimensions, may be introduced from the rear of the patient, with the result that it a single operation may be called upon, during which these prostheses are implanted at the same time as the damping member.

To provide a single prosthesis, associated with a single extra-discal damping member, both offset on the same side of the principal axis of the vertebral chain, makes it possible to overcome asymmetrical collapses of the intervertebral space, seen from behind. Such asymmetrical collapses may also be obviated by employing two prostheses of different heights, disposed on either side of the principal axis of the vertebral chain.

The invention claimed is:

1. An intervertebral stabilization apparatus, comprising:
   an implant operable to be inserted at least partially between adjacent vertebral bodies and maintain at least one mutual degree of freedom of the vertebral bodies when inserted therebetween; and
   at least one extra-discal member operable to be disposed posteriorly to said implant when said implant is at least partially positioned between the vertebral bodies, said at least one extra-discal member further being configured to be coupled with each of the vertebral bodies and including a first anchor engaging portion attached to a first bone screw and having a longitudinal axis aligned with a longitudinal axis of the first bone screw, a second anchor engaging portion attached to a second bone screw and having a longitudinal axis aligned with a longitudinal axis of the second bone screw, and a dampening member positioned between said longitudinal axes of said first and second anchor engaging portions, said dampening member being configured to dampen displacement between the vertebral bodies at least in response to intervertebral flexion when said at least one extra-discal member is disposed posteriorly to said implant.

2. The apparatus of claim 1, wherein said implant includes:
   an upper element including a superior surface engageable with an inferior surface of an upper vertebral body and an inferior surface positioned opposite said superior surface; and
   a lower element including an inferior surface engageable with a superior surface of a lower vertebral body and a superior surface positioned opposite said inferior surface.

3. The apparatus of claim 2, wherein said implant includes an elastic core positioned between said upper element and said lower element.

4. The apparatus of claim 3, wherein said implant includes a distance between said upper element and said lower element, said distance increasing toward an anterior side of the implant.

5. An intervertebral stabilization apparatus, comprising:
   a first implant positionable at least partially between adjacent vertebral bodies, said first implant including means for providing at least one mutual degree of freedom of the vertebral bodies; and
   a first extra-discal member positionable posteriorly to said first implant, said first extra-discal member being configured to be coupled with each of the vertebral bodies and including a first anchor engaging portion attached to a first bone screw and having a longitudinal axis aligned with a longitudinal axis of the first bone screw, a second anchor engaging portion attached to a second bone screw and having a longitudinal axis aligned with a longitudinal axis of the second bone screw, and means for dampening displacement between the vertebral bodies at least in response to intervertebral flexion when said first extra-discal member is positioned posteriorly to said implant, said means for dampening displacement being positioned between said longitudinal axes of said first and second anchor engaging portions.

6. A method to stabilize adjacent vertebrae of a patient's spine, comprising:
   inserting a first implant at least partially between the adjacent vertebrae;
   maintaining at least one mutual degree of freedom between the adjacent vertebrae after inserting the first implant; and
   coupling a first extra-discal member to each of the vertebrae posterior to the first implant, said first extra-discal member including a first anchor engaging portion attached to a first bone screw and having a longitudinal axis aligned with a longitudinal axis of the first bone screw, a second anchor engaging portion attached to a second bone screw and having a longitudinal axis aligned with a longitudinal axis of the second bone screw, and a dampening member positioned between said longitudinal axes of said first and second anchor engaging portions, said dampening member being configured to dampen displacement between the vertebral bodies at least in response to intervertebral flexion.

* * * * *